(12) United States Patent
McCaulley et al.

(10) Patent No.: US 9,585,597 B2
(45) Date of Patent: Mar. 7, 2017

(54) PATIENT SPECIFIC INSTRUMENTATION WITH MEMS IN SURGERY

(71) Applicants: ORTHOSOFT, INC., Montreal (CA); ZIMMER, INC., Warsaw, IN (US)

(72) Inventors: Jeffrey A. McCaulley, Warsaw, IN (US); Louis-Philippe Amiot, Hampstead (CA)

(73) Assignee: ZIMMER, INC., Warsaw, IN (US)

( * ) Notice: Subject to any disclaimer, the term of this patent is extended or adjusted under 35 U.S.C. 154(b) by 736 days.

(21) Appl. No.: 13/949,697

(22) Filed: Jul. 24, 2013

(65) Prior Publication Data

US 2014/0031672 A1 Jan. 30, 2014

Related U.S. Application Data

(60) Provisional application No. 61/675,242, filed on Jul. 24, 2012.

(51) Int. Cl.
  *A61B 17/15* (2006.01)
  *A61B 5/06* (2006.01)
  (Continued)

(52) U.S. Cl.
  CPC .............. *A61B 5/06* (2013.01); *A61B 5/1114* (2013.01); *A61B 5/6878* (2013.01); *A61B 17/15* (2013.01);
  (Continued)

(58) Field of Classification Search
  CPC ..... A61B 17/15; A61B 17/154; A61B 17/155; A61B 17/157; A61B 17/17;
  (Continued)

(56) References Cited

U.S. PATENT DOCUMENTS

| 4,841,975 A | 6/1989 | Woolson |
| 5,098,383 A | 3/1992 | Hemmy et al. |

(Continued)

FOREIGN PATENT DOCUMENTS

| AU | 2004293091 A1 | 6/2005 |
| AU | 2004293104 A1 | 6/2005 |

(Continued)

OTHER PUBLICATIONS

Taylor et al, "Computer-Integrated Surgery, Technology and Clinical Applications", The MIT Press, Cambridge, MA, London, UK, pp. 451-463.

(Continued)

*Primary Examiner* — Christian Sevilla
*Assistant Examiner* — Eric S Gibson
(74) *Attorney, Agent, or Firm* — Norton Rose Fulbright Canada LLP

(57) ABSTRACT

An assembly of a patient specific instrument and tracking system comprises a patient specific instrument having a body with a patient specific contact surface negatively shaped relative to a corresponding surface of a bone for complementary contact therewith. An inertial sensor unit with a preset orientation is connected to the body in a planned connection configuration, such that a geometrical relation between the contact surface and the inertial sensor unit is known. A tracking system has a tracking processor connected to the inertial sensor unit, a user interface, and bone orientation data related to the patient specific contact surface, the tracking processor producing orientation tracking data for the bone using the geometrical relation and the bone orientation data when the preset orientation of the inertial sensor unit is initialized, to output the orientation tracking data on the user interface.

5 Claims, 2 Drawing Sheets

(51) Int. Cl.
*A61B 5/00* (2006.01)
*A61B 5/11* (2006.01)
*A61B 6/00* (2006.01)
*A61B 6/03* (2006.01)

(52) U.S. Cl.
CPC .............. *A61B 34/20* (2016.02); *A61B 6/032* (2013.01); *A61B 6/505* (2013.01); *A61B 2034/102* (2016.02); *A61B 2034/105* (2016.02); *A61B 2034/108* (2016.02); *A61B 2034/2048* (2016.02); *A61B 2505/05* (2013.01)

(58) Field of Classification Search
CPC ............ A61B 17/1707; A61B 17/1739; A61B 17/1742; A61B 17/1746; A61B 17/175; A61B 17/1753; A61B 17/1757; A61B 17/176; A61B 17/1764; A61B 2017/1771; A61B 2017/1775; A61B 2017/1778; A61B 2017/1782; A61B 2017/1785; A61B 2017/1789; A61B 2017/1792
USPC .......................................... 606/86 R–89, 130
See application file for complete search history.

(56) References Cited

U.S. PATENT DOCUMENTS

| | | | | |
|---|---|---|---|---|
| 5,343,391 | A * | 8/1994 | Mushabac | A61C 13/0004 433/72 |
| 5,490,854 | A | 2/1996 | Fisher et al. | |
| 5,768,134 | A | 6/1998 | Swaelens et al. | |
| 5,871,018 | A | 2/1999 | Delp et al. | |
| 5,916,219 | A | 6/1999 | Matsuno et al. | |
| 6,491,700 | B1 * | 12/2002 | Lavallee | 606/130 |
| 7,357,057 | B2 | 4/2008 | Chiang | |
| 7,468,075 | B2 | 12/2008 | Lang et al. | |
| 7,510,557 | B1 | 3/2009 | Bonutti | |
| 7,534,263 | B2 | 5/2009 | Burdulis | |
| 7,618,451 | B2 | 11/2009 | Berez et al. | |
| 7,634,119 | B2 | 12/2009 | Tsougarakis et al. | |
| 7,717,956 | B2 | 5/2010 | Lang | |
| 7,796,791 | B2 | 9/2010 | Tsougarakis et al. | |
| 7,799,077 | B2 | 9/2010 | Lang et al. | |
| 7,806,896 | B1 | 10/2010 | Bonutti | |
| 7,806,897 | B1 | 10/2010 | Bonutti | |
| 7,967,868 | B2 | 6/2011 | White et al. | |
| 7,981,158 | B2 | 7/2011 | Fitz et al. | |
| 8,062,302 | B2 | 11/2011 | Lang et al. | |
| 8,066,708 | B2 | 11/2011 | Lang et al. | |
| 8,070,752 | B2 | 12/2011 | Metzger et al. | |
| 8,077,950 | B2 | 12/2011 | Tsougarakis et al. | |
| 8,083,745 | B2 | 12/2011 | Lang et al. | |
| 8,092,465 | B2 | 1/2012 | Metzger et al. | |
| 8,094,900 | B2 | 1/2012 | Steines et al. | |
| 8,105,330 | B2 | 1/2012 | Fitz et al. | |
| 8,122,582 | B2 | 2/2012 | Burdulis, Jr. et al. | |
| 8,133,234 | B2 | 3/2012 | Meridew et al. | |
| 8,160,345 | B2 | 4/2012 | Pavlovskaia et al. | |
| 8,175,683 | B2 | 5/2012 | Roose | |
| 8,221,430 | B2 | 7/2012 | Park et al. | |
| 8,234,097 | B2 | 7/2012 | Steines et al. | |
| 8,241,293 | B2 | 8/2012 | Stone et al. | |
| 8,282,646 | B2 | 10/2012 | Schoenefeld et al. | |
| 8,298,237 | B2 | 10/2012 | Schoenefeld | |
| 8,337,501 | B2 | 12/2012 | Fitz et al. | |
| 8,337,507 | B2 | 12/2012 | Lang et al. | |
| 8,343,218 | B2 | 1/2013 | Lang et al. | |
| 8,366,771 | B2 | 2/2013 | Burdulis et al. | |
| 8,377,129 | B2 | 2/2013 | Fitz et al. | |
| 8,439,926 | B2 | 5/2013 | Bojarski et al. | |
| 8,454,619 | B1 * | 6/2013 | Head | A61B 17/1746 606/91 |
| 8,460,304 | B2 | 6/2013 | Fitz et al. | |
| 8,480,754 | B2 | 7/2013 | Bojarski et al. | |
| 8,500,740 | B2 | 8/2013 | Bojarski et al. | |
| 8,529,568 | B2 | 9/2013 | Bouadi | |
| 8,529,630 | B2 | 9/2013 | Bojarski | |
| 8,545,569 | B2 | 10/2013 | Fitz et al. | |
| 8,551,099 | B2 | 10/2013 | Lang | |
| 8,551,102 | B2 | 10/2013 | Fitz et al. | |
| 8,551,103 | B2 | 10/2013 | Fitz et al. | |
| 8,551,169 | B2 | 10/2013 | Fitz et al. | |
| 8,556,906 | B2 | 10/2013 | Fitz et al. | |
| 8,556,907 | B2 | 10/2013 | Fitz et al. | |
| 8,556,971 | B2 | 10/2013 | Lang | |
| 8,556,983 | B2 | 10/2013 | Bojarski et al. | |
| 8,561,278 | B2 | 10/2013 | Fitz et al. | |
| 8,562,611 | B2 | 10/2013 | Fitz et al. | |
| 8,562,618 | B2 | 10/2013 | Fitz et al. | |
| 8,568,479 | B2 | 10/2013 | Fitz et al. | |
| 8,568,480 | B2 | 10/2013 | Fitz et al. | |
| 8,570,274 | B1 * | 10/2013 | Mcintosh | G06F 1/169 345/158 |
| 8,585,708 | B2 | 11/2013 | Fitz et al. | |
| 8,617,172 | B2 | 12/2013 | Fitz et al. | |
| 8,617,242 | B2 | 12/2013 | Philipp | |
| 8,623,026 | B2 | 1/2014 | Wong et al. | |
| 8,634,617 | B2 | 1/2014 | Tsougarakis et al. | |
| 8,638,998 | B2 | 1/2014 | Steines et al. | |
| 8,641,716 | B2 | 2/2014 | Fitz et al. | |
| 8,657,827 | B2 | 2/2014 | Fitz et al. | |
| 8,682,052 | B2 | 3/2014 | Fitz et al. | |
| 8,696,675 | B2 * | 4/2014 | Boutin | A61B 19/2203 600/587 |
| 8,790,351 | B2 * | 7/2014 | Paradis | A61B 19/5244 606/102 |
| 9,005,207 | B2 * | 4/2015 | Dodds | A61B 17/155 606/87 |
| 2003/0055502 | A1 | 3/2003 | Lang et al. | |
| 2003/0208296 | A1 * | 11/2003 | Brisson | A61B 90/10 700/117 |
| 2003/0216669 | A1 * | 11/2003 | Lang | A61B 5/4528 600/587 |
| 2004/0039396 | A1 * | 2/2004 | Couture | A61B 17/154 606/87 |
| 2004/0133276 | A1 | 7/2004 | Lang et al. | |
| 2004/0138754 | A1 | 7/2004 | Lang et al. | |
| 2004/0147927 | A1 | 7/2004 | Tsougarakis et al. | |
| 2004/0153079 | A1 | 8/2004 | Tsougarakis et al. | |
| 2004/0204644 | A1 | 10/2004 | Tsougarakis et al. | |
| 2004/0204760 | A1 | 10/2004 | Fitz et al. | |
| 2004/0236424 | A1 * | 11/2004 | Berez | A61B 5/1077 623/14.12 |
| 2005/0085720 | A1 * | 4/2005 | Jascob | A61B 5/06 600/424 |
| 2005/0203528 | A1 * | 9/2005 | Couture | A61B 17/154 606/86 R |
| 2005/0234461 | A1 | 10/2005 | Burdulis et al. | |
| 2005/0267584 | A1 | 12/2005 | Burdulis et al. | |
| 2006/0111722 | A1 | 5/2006 | Bouadi | |
| 2006/0142657 | A1 * | 6/2006 | Quaid | A61B 17/1764 600/424 |
| 2007/0083266 | A1 | 4/2007 | Lang | |
| 2007/0100462 | A1 | 5/2007 | Lang et al. | |
| 2007/0156171 | A1 | 7/2007 | Lang et al. | |
| 2007/0157783 | A1 | 7/2007 | Chiang | |
| 2007/0198022 | A1 * | 8/2007 | Lang | A61B 17/154 606/88 |
| 2007/0226986 | A1 | 10/2007 | Park et al. | |
| 2007/0233141 | A1 | 10/2007 | Park et al. | |
| 2007/0233269 | A1 | 10/2007 | Steines et al. | |
| 2007/0250169 | A1 | 10/2007 | Lang | |
| 2008/0114370 | A1 | 5/2008 | Schoenefeld | |
| 2008/0147072 | A1 | 6/2008 | Park et al. | |
| 2008/0161815 | A1 | 7/2008 | Schoenefeld et al. | |
| 2008/0195109 | A1 * | 8/2008 | Hunter | A61B 17/155 606/87 |
| 2008/0195216 | A1 | 8/2008 | Philipp | |
| 2008/0243127 | A1 * | 10/2008 | Lang | A61B 5/4528 606/87 |
| 2008/0275452 | A1 | 11/2008 | Lang et al. | |
| 2008/0281328 | A1 | 11/2008 | Lang et al. | |
| 2008/0281329 | A1 | 11/2008 | Fitz et al. | |

(56) References Cited

U.S. PATENT DOCUMENTS

| | | |
|---|---|---|
| 2008/0281426 A1 | 11/2008 | Fitz et al. |
| 2008/0287954 A1 | 11/2008 | Kunz et al. |
| 2009/0024131 A1 | 1/2009 | Metzger et al. |
| 2009/0087276 A1* | 4/2009 | Rose .................... A61B 17/155 409/79 |
| 2009/0088674 A1* | 4/2009 | Caillouette ............ A61B 5/061 602/26 |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0093816 A1 | 4/2009 | Roose et al. |
| 2009/0099567 A1 | 4/2009 | Zajac |
| 2009/0110498 A1 | 4/2009 | Park et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0157083 A1 | 6/2009 | Park et al. |
| 2009/0222014 A1 | 9/2009 | Bojarski et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228113 A1 | 9/2009 | Lang et al. |
| 2009/0247863 A1* | 10/2009 | Proulx ................ A61B 19/5244 600/426 |
| 2009/0248044 A1* | 10/2009 | Amiot ................ A61B 19/5244 606/130 |
| 2009/0254093 A1 | 10/2009 | White et al. |
| 2009/0254098 A1* | 10/2009 | Christian ...................... 606/130 |
| 2009/0270868 A1 | 10/2009 | Park et al. |
| 2009/0274350 A1* | 11/2009 | Pavlovskaia ............ G06K 9/32 382/128 |
| 2009/0276045 A1 | 11/2009 | Lang |
| 2009/0306676 A1 | 12/2009 | Lang et al. |
| 2009/0307893 A1 | 12/2009 | Burdulis, Jr. et al. |
| 2009/0312805 A1 | 12/2009 | Lang et al. |
| 2010/0023015 A1 | 1/2010 | Park |
| 2010/0042105 A1 | 2/2010 | Park et al. |
| 2010/0049195 A1 | 2/2010 | Park et al. |
| 2010/0054572 A1 | 3/2010 | Tsougarakis et al. |
| 2010/0076563 A1* | 3/2010 | Otto .................... A61B 5/103 623/20.14 |
| 2010/0082035 A1 | 4/2010 | Keefer et al. |
| 2010/0087829 A1 | 4/2010 | Metzger et al. |
| 2010/0152741 A1* | 6/2010 | Park .................... A61B 17/155 606/89 |
| 2010/0152782 A1 | 6/2010 | Stone et al. |
| 2010/0160917 A1 | 6/2010 | Fitz et al. |
| 2010/0168754 A1 | 7/2010 | Fitz et al. |
| 2010/0174376 A1 | 7/2010 | Lang et al. |
| 2010/0185202 A1 | 7/2010 | Lester et al. |
| 2010/0191244 A1* | 7/2010 | White .................... A61B 17/155 606/88 |
| 2010/0212138 A1 | 8/2010 | Carroll et al. |
| 2010/0217270 A1 | 8/2010 | Polinski et al. |
| 2010/0217338 A1 | 8/2010 | Carroll et al. |
| 2010/0228257 A1 | 9/2010 | Bonutti |
| 2010/0234849 A1 | 9/2010 | Bouadi |
| 2010/0249791 A1* | 9/2010 | Roche .................. A61B 5/1076 606/90 |
| 2010/0256479 A1 | 10/2010 | Park et al. |
| 2010/0262150 A1 | 10/2010 | Lian |
| 2010/0274534 A1 | 10/2010 | Steines et al. |
| 2010/0281678 A1 | 11/2010 | Burdulis, Jr. et al. |
| 2010/0286700 A1 | 11/2010 | Snider et al. |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305573 A1 | 12/2010 | Fitz et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0324692 A1* | 12/2010 | Uthgenannt ........ A61F 2/30942 623/20.35 |
| 2010/0329530 A1 | 12/2010 | Lang et al. |
| 2011/0015636 A1 | 1/2011 | Katrana et al. |
| 2011/0015637 A1 | 1/2011 | De Smedt et al. |
| 2011/0015639 A1 | 1/2011 | Metzger et al. |
| 2011/0029091 A1* | 2/2011 | Bojarski ............ A61F 2/30942 623/20.32 |
| 2011/0029093 A1 | 2/2011 | Bojarski et al. |
| 2011/0040168 A1 | 2/2011 | Arnaud et al. |
| 2011/0054478 A1 | 3/2011 | Vanasse et al. |
| 2011/0060341 A1 | 3/2011 | Angibaud et al. |
| 2011/0066193 A1 | 3/2011 | Lang et al. |
| 2011/0066245 A1 | 3/2011 | Lang et al. |
| 2011/0071533 A1 | 3/2011 | Metzger et al. |
| 2011/0071581 A1 | 3/2011 | Lang et al. |
| 2011/0071645 A1 | 3/2011 | Bojarski et al. |
| 2011/0071802 A1 | 3/2011 | Bojarski et al. |
| 2011/0087332 A1* | 4/2011 | Bojarski ............ A61B 17/155 623/20.32 |
| 2011/0092977 A1 | 4/2011 | Salehi et al. |
| 2011/0093108 A1 | 4/2011 | Ashby et al. |
| 2011/0106093 A1 | 5/2011 | Romano et al. |
| 2011/0144760 A1 | 6/2011 | Wong et al. |
| 2011/0160583 A1* | 6/2011 | Roche ................ A61B 19/5244 600/438 |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0184419 A1 | 7/2011 | Meridew et al. |
| 2011/0196377 A1* | 8/2011 | Hodorek ............ A61B 17/155 606/87 |
| 2011/0208256 A1* | 8/2011 | Zuhars .................. A61B 19/50 606/86 R |
| 2011/0213221 A1* | 9/2011 | Roche .................. A61B 5/0031 600/301 |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213376 A1 | 9/2011 | Maxson et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0214279 A1 | 9/2011 | Park et al. |
| 2011/0218539 A1 | 9/2011 | Fitz et al. |
| 2011/0218545 A1 | 9/2011 | Catanzarite et al. |
| 2011/0218584 A1 | 9/2011 | Fitz et al. |
| 2011/0224674 A1 | 9/2011 | White et al. |
| 2011/0230888 A1 | 9/2011 | Lang et al. |
| 2011/0238073 A1 | 9/2011 | Lang et al. |
| 2011/0245835 A1 | 10/2011 | Dodds et al. |
| 2011/0266265 A1 | 11/2011 | Lang |
| 2011/0275957 A1 | 11/2011 | Bhandari |
| 2011/0282473 A1* | 11/2011 | Pavlovskaia ............ A61B 19/50 700/98 |
| 2011/0295329 A1 | 12/2011 | Fitz et al. |
| 2011/0295378 A1 | 12/2011 | Bojarski et al. |
| 2011/0313423 A1 | 12/2011 | Lang et al. |
| 2011/0313424 A1 | 12/2011 | Bono et al. |
| 2011/0319897 A1 | 12/2011 | Lang et al. |
| 2011/0319900 A1 | 12/2011 | Lang et al. |
| 2012/0010711 A1 | 1/2012 | Antonyshyn et al. |
| 2012/0022406 A1* | 1/2012 | Hladio .................. A61F 2/4609 600/587 |
| 2012/0029389 A1* | 2/2012 | Amiot .......................... 600/595 |
| 2012/0029520 A1 | 2/2012 | Lang et al. |
| 2012/0041445 A1 | 2/2012 | Roose et al. |
| 2012/0041446 A1* | 2/2012 | Wong .................. A61B 17/1703 606/96 |
| 2012/0065640 A1 | 3/2012 | Metzger et al. |
| 2012/0066892 A1 | 3/2012 | Lang et al. |

(56) References Cited

U.S. PATENT DOCUMENTS

| | | | |
|---|---|---|---|
| 2012/0071881 A1 | 3/2012 | Lang et al. | |
| 2012/0071882 A1 | 3/2012 | Lang et al. | |
| 2012/0071883 A1 | 3/2012 | Lang et al. | |
| 2012/0072185 A1 | 3/2012 | Lang et al. | |
| 2012/0078254 A1* | 3/2012 | Ashby | A61B 17/1764 606/79 |
| 2012/0078258 A1 | 3/2012 | Lo et al. | |
| 2012/0078259 A1 | 3/2012 | Meridew | |
| 2012/0093377 A1 | 4/2012 | Tsougarakis et al. | |
| 2012/0101503 A1 | 4/2012 | Lang et al. | |
| 2012/0109138 A1 | 5/2012 | Meridew et al. | |
| 2012/0109228 A1* | 5/2012 | Boyer | A61B 17/154 606/86 R |
| 2012/0116203 A1* | 5/2012 | Vancraen | A61F 2/30942 600/407 |
| 2012/0116562 A1* | 5/2012 | Agnihotri | A61B 17/155 700/98 |
| 2012/0123422 A1 | 5/2012 | Agnihotri et al. | |
| 2012/0123423 A1 | 5/2012 | Fryman | |
| 2012/0130382 A1 | 5/2012 | Iannotti et al. | |
| 2012/0130687 A1 | 5/2012 | Otto et al. | |
| 2012/0141034 A1 | 6/2012 | Iannotti et al. | |
| 2012/0143197 A1 | 6/2012 | Lang et al. | |
| 2012/0143198 A1* | 6/2012 | Boyer | A61B 17/151 606/87 |
| 2012/0151730 A1 | 6/2012 | Fitz et al. | |
| 2012/0157887 A1* | 6/2012 | Fanson | A61B 19/5244 600/595 |
| 2012/0158001 A1 | 6/2012 | Burdulis, Jr. et al. | |
| 2012/0165820 A1 | 6/2012 | De Smedt et al. | |
| 2012/0172884 A1 | 7/2012 | Zheng et al. | |
| 2012/0191205 A1 | 7/2012 | Bojarski et al. | |
| 2012/0191420 A1 | 7/2012 | Bojarski et al. | |
| 2012/0192401 A1 | 8/2012 | Pavlovskaia et al. | |
| 2012/0197260 A1 | 8/2012 | Fitz et al. | |
| 2012/0197408 A1 | 8/2012 | Lang et al. | |
| 2012/0201440 A1 | 8/2012 | Steines et al. | |
| 2012/0209276 A1 | 8/2012 | Schuster | |
| 2012/0209394 A1 | 8/2012 | Bojarski et al. | |
| 2012/0215226 A1 | 8/2012 | Bonutti | |
| 2012/0220859 A1* | 8/2012 | Amiot | A61B 17/157 600/424 |
| 2012/0221008 A1 | 8/2012 | Carroll et al. | |
| 2012/0226283 A1* | 9/2012 | Meridew | A61B 17/1659 606/81 |
| 2012/0232669 A1 | 9/2012 | Bojarski et al. | |
| 2012/0232670 A1 | 9/2012 | Bojarski et al. | |
| 2012/0232671 A1 | 9/2012 | Bojarski | |
| 2012/0232834 A1* | 9/2012 | Roche | 702/150 |
| 2012/0239045 A1 | 9/2012 | Li | |
| 2012/0245647 A1* | 9/2012 | Kunz | A61B 17/1746 606/86 R |
| 2012/0245699 A1 | 9/2012 | Lang et al. | |
| 2012/0265208 A1 | 10/2012 | Smith | |
| 2012/0265496 A1* | 10/2012 | Mahfouz | A61B 17/14 703/1 |
| 2012/0271366 A1 | 10/2012 | Katrana et al. | |
| 2012/0276509 A1 | 11/2012 | Iannotti et al. | |
| 2012/0277751 A1 | 11/2012 | Catanzarite et al. | |
| 2012/0289965 A1* | 11/2012 | Gelaude | A61B 17/15 606/87 |
| 2012/0289966 A1 | 11/2012 | Fitz et al. | |
| 2012/0290019 A1* | 11/2012 | Chellaoui | A61B 17/157 606/86 R |
| 2012/0296337 A1 | 11/2012 | Fitz et al. | |
| 2012/0323244 A1* | 12/2012 | Cheal | A61B 17/155 606/87 |
| 2013/0006250 A1* | 1/2013 | Metzger | A61B 17/155 606/87 |
| 2013/0006251 A1* | 1/2013 | Aram | A61B 17/1764 606/88 |
| 2013/0018379 A1 | 1/2013 | Fitz et al. | |
| 2013/0018380 A1 | 1/2013 | Fitz et al. | |
| 2013/0018464 A1 | 1/2013 | Fitz et al. | |
| 2013/0023884 A1 | 1/2013 | Fitz et al. | |
| 2013/0024000 A1 | 1/2013 | Bojarski et al. | |
| 2013/0030419 A1 | 1/2013 | Fitz et al. | |
| 2013/0030441 A1 | 1/2013 | Fitz et al. | |
| 2013/0053854 A1* | 2/2013 | Schoenefeld | A61B 17/1757 606/87 |
| 2013/0079781 A1 | 3/2013 | Fitz et al. | |
| 2013/0079876 A1 | 3/2013 | Fitz et al. | |
| 2013/0081247 A1 | 4/2013 | Fitz et al. | |
| 2013/0085500 A1* | 4/2013 | Meridew | A61B 17/15 606/89 |
| 2013/0096562 A1 | 4/2013 | Fitz et al. | |
| 2013/0103363 A1 | 4/2013 | Lang et al. | |
| 2013/0110471 A1 | 5/2013 | Lang et al. | |
| 2013/0123792 A1 | 5/2013 | Fitz et al. | |
| 2013/0138111 A1* | 5/2013 | Aram | A61B 17/157 606/88 |
| 2013/0150862 A1* | 6/2013 | Aram | A61B 17/157 606/88 |
| 2013/0184713 A1 | 7/2013 | Bojarski et al. | |
| 2013/0190768 A1* | 7/2013 | Aram | A61B 17/1764 606/88 |
| 2013/0197870 A1 | 8/2013 | Steines et al. | |
| 2013/0211409 A1 | 8/2013 | Burdulis, Jr. et al. | |
| 2013/0211410 A1 | 8/2013 | Landes et al. | |
| 2013/0211411 A1* | 8/2013 | Tuke | A61B 17/155 606/88 |
| 2013/0211531 A1 | 8/2013 | Steines et al. | |
| 2013/0231672 A1* | 9/2013 | Paradis | A61F 2/4657 606/91 |
| 2013/0236874 A1* | 9/2013 | Iannotti | A61B 17/17 434/274 |
| 2013/0245803 A1 | 9/2013 | Lang | |
| 2013/0253522 A1 | 9/2013 | Bojarski et al. | |
| 2013/0274778 A1* | 10/2013 | Mercier | A61B 17/1739 606/172 |
| 2013/0289570 A1 | 10/2013 | Chao | |
| 2013/0296874 A1 | 11/2013 | Chao | |
| 2013/0297031 A1 | 11/2013 | Hafez | |
| 2013/0317511 A1 | 11/2013 | Bojarski et al. | |
| 2013/0331850 A1 | 12/2013 | Bojarski et al. | |
| 2014/0005792 A1 | 1/2014 | Lang et al. | |
| 2014/0029814 A1 | 1/2014 | Fitz et al. | |
| 2014/0031672 A1* | 1/2014 | McCaulley | A61B 5/06 600/424 |
| 2014/0031826 A1 | 1/2014 | Bojarski et al. | |
| 2014/0031829 A1* | 1/2014 | Paradis | A61B 19/46 606/102 |
| 2014/0039631 A1 | 2/2014 | Bojarski et al. | |
| 2014/0058396 A1 | 2/2014 | Fitz et al. | |
| 2014/0058397 A1 | 2/2014 | Fitz et al. | |
| 2014/0066935 A1 | 3/2014 | Fitz et al. | |
| 2014/0066936 A1 | 3/2014 | Fitz et al. | |
| 2014/0074441 A1 | 3/2014 | Fitz et al. | |
| 2014/0086780 A1 | 3/2014 | Miller et al. | |
| 2014/0107655 A1* | 4/2014 | Song | A61B 17/157 606/88 |
| 2014/0135773 A1* | 5/2014 | Stein | G06F 19/3406 606/80 |
| 2014/0142580 A1* | 5/2014 | Aram | A61B 17/155 606/89 |
| 2014/0188240 A1* | 7/2014 | Lang | A61F 2/30942 623/22.12 |
| 2014/0200902 A1* | 7/2014 | Aram | A61B 17/155 705/2 |
| 2014/0208578 A1* | 7/2014 | Linderman | A61B 17/155 29/592 |
| 2014/0257309 A1* | 9/2014 | Aram | A61B 17/154 606/88 |
| 2014/0276855 A1* | 9/2014 | de la Barrera | G06F 19/3412 606/87 |
| 2014/0276864 A1* | 9/2014 | Aghazadeh | A61B 17/1764 606/88 |
| 2014/0276867 A1* | 9/2014 | Kelley | A61B 17/1746 606/89 |
| 2014/0277542 A1* | 9/2014 | Stein | A61B 17/154 623/20.32 |

(56) References Cited

U.S. PATENT DOCUMENTS

| | | | | |
|---|---|---|---|---|
| 2015/0088141 A1* | 3/2015 | Uthgenannt | ....... | A61B 17/1675 606/88 |
| 2015/0088143 A1* | 3/2015 | Lipman | .............. | A61B 17/1764 606/88 |
| 2016/0022370 A1* | 1/2016 | Pavlovskaia | ........... | A61B 19/50 703/1 |
| 2016/0045317 A1* | 2/2016 | Lang | ................... | A61F 2/30942 700/98 |

FOREIGN PATENT DOCUMENTS

| | | |
|---|---|---|
| AU | 2005309692 A1 | 6/2006 |
| AU | 2005311558 A1 | 6/2006 |
| AU | 2002310193 B2 | 3/2007 |
| AU | 2006297137 A1 | 4/2007 |
| AU | 2002310193 B8 | 5/2007 |
| AU | 2007202573 A1 | 6/2007 |
| AU | 2007212033 A1 | 8/2007 |
| AU | 2007226924 A1 | 9/2007 |
| AU | 2009221773 A1 | 9/2009 |
| AU | 2009246474 A1 | 11/2009 |
| AU | 2010201200 A1 | 4/2010 |
| AU | 2011203237 A1 | 7/2011 |
| AU | 2010217903 A1 | 9/2011 |
| AU | 2010236263 A1 | 11/2011 |
| AU | 2010264466 A1 | 2/2012 |
| AU | 2010289706 A1 | 3/2012 |
| AU | 2010315099 A1 | 5/2012 |
| AU | 2010327987 A1 | 6/2012 |
| AU | 2011203237 B2 | 10/2012 |
| AU | 2012216829 A1 | 10/2012 |
| AU | 2012217654 A1 | 10/2013 |
| AU | 2007212033 B2 | 1/2014 |
| AU | 2014200073 A1 | 1/2014 |
| AU | 2012289973 A1 | 3/2014 |
| AU | 2012296556 A1 | 3/2014 |
| CA | 2501041 A1 | 4/2004 |
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2804883 A1 | 6/2005 |
| CA | 2588907 A1 | 6/2006 |
| CA | 2590534 A1 | 6/2006 |
| CA | 2623834 A1 | 4/2007 |
| CA | 2641241 A1 | 8/2007 |
| CA | 2646288 A1 | 9/2007 |
| CA | 2717760 A1 | 9/2009 |
| CA | 2765499 A1 | 12/2010 |
| CA | 2771573 A1 | 3/2011 |
| CA | 2779283 A1 | 5/2011 |
| CA | 2782137 A1 | 6/2011 |
| CA | 2546965 C | 3/2013 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 101384230 A | 3/2009 |
| CN | 101442960 A | 5/2009 |
| CN | 100502808 C | 6/2009 |
| CN | 102006841 A | 4/2011 |
| CN | 102125448 A | 7/2011 |
| CN | 102405032 A | 4/2012 |
| CN | 102448394 A | 5/2012 |
| CN | 101420911 B | 7/2012 |
| CN | 102599960 A | 7/2012 |
| CN | 1913844 B | 9/2012 |
| CN | 102711670 A | 10/2012 |
| CN | 102724934 A | 10/2012 |
| CN | 102805677 A | 12/2012 |
| CN | 1729483 B | 10/2013 |
| CN | 103476363 A | 12/2013 |
| DE | 60336002 D1 | 3/2011 |
| DE | 60239674 D1 | 5/2011 |
| DE | 602004032166 D1 | 5/2011 |
| DE | 602005027391 D1 | 5/2011 |
| EP | 1555962 A1 | 7/2005 |
| EP | 1558181 A1 | 8/2005 |
| EP | 1567985 A2 | 8/2005 |
| EP | 1575460 A2 | 9/2005 |
| EP | 1686930 A1 | 8/2006 |
| EP | 1686931 A1 | 8/2006 |
| EP | 1389980 A4 | 4/2007 |
| EP | 1814491 A1 | 8/2007 |
| EP | 1833387 A1 | 9/2007 |
| EP | 1686930 A4 | 10/2007 |
| EP | 1686931 A4 | 1/2008 |
| EP | 1928359 A2 | 6/2008 |
| EP | 1951136 A1 | 8/2008 |
| EP | 1981409 A2 | 10/2008 |
| EP | 1996121 A2 | 12/2008 |
| EP | 2114312 A2 | 11/2009 |
| EP | 2124764 A1 | 12/2009 |
| EP | 1928359 A4 | 10/2010 |
| EP | 2259753 A1 | 12/2010 |
| EP | 2265199 A1 | 12/2010 |
| EP | 1555962 B1 | 2/2011 |
| EP | 2292188 A2 | 3/2011 |
| EP | 2292189 A2 | 3/2011 |
| EP | 1389980 B1 | 4/2011 |
| EP | 1686930 B1 | 4/2011 |
| EP | 1833387 B1 | 4/2011 |
| EP | 2303193 A1 | 4/2011 |
| EP | 2316357 A1 | 5/2011 |
| EP | 2324799 A2 | 5/2011 |
| EP | 2335654 A1 | 6/2011 |
| EP | 2403434 A1 | 1/2012 |
| EP | 2405865 A2 | 1/2012 |
| EP | 2419035 A1 | 2/2012 |
| EP | 2265199 A4 | 3/2012 |
| EP | 2303193 A4 | 3/2012 |
| EP | 2259753 A4 | 4/2012 |
| EP | 2292188 A3 | 5/2012 |
| EP | 2292189 A3 | 5/2012 |
| EP | 2445451 A1 | 5/2012 |
| EP | 2470126 A1 | 7/2012 |
| EP | 2496183 A2 | 9/2012 |
| EP | 2509539 A2 | 10/2012 |
| EP | 2512381 A2 | 10/2012 |
| EP | 2324799 A3 | 1/2013 |
| EP | 2419035 A4 | 1/2013 |
| EP | 2445451 A4 | 3/2013 |
| EP | 2403434 A4 | 4/2013 |
| EP | 2591756 A1 | 5/2013 |
| EP | 2496183 A4 | 12/2013 |
| EP | 2512381 A4 | 12/2013 |
| EP | 2649951 A2 | 12/2013 |
| EP | 2649951 A3 | 12/2013 |
| EP | 2671520 A3 | 12/2013 |
| EP | 2671521 A3 | 12/2013 |
| EP | 2671522 A3 | 12/2013 |
| EP | 2114312 B1 | 1/2014 |
| EP | 2710967 A2 | 3/2014 |
| GB | 2484042 A | 3/2012 |
| GB | 2489884 A | 10/2012 |
| GB | 201213674 | 10/2012 |
| GB | 2484042 B | 3/2014 |
| HK | 1059882 A1 | 8/2011 |
| HK | 1072710 A1 | 8/2011 |
| HK | 1087324 A1 | 11/2011 |
| HK | 1104776 A1 | 11/2011 |
| JP | 2006510403 A | 3/2006 |
| JP | 2007514470 A | 6/2007 |
| JP | 2011519713 A | 7/2011 |
| JP | 2011224384 A | 11/2011 |
| JP | 2012091033 A | 5/2012 |
| JP | 2012176318 A | 9/2012 |
| JP | 5053515 B2 | 10/2012 |
| JP | 2012187415 A | 10/2012 |
| JP | 2012523897 A | 10/2012 |
| JP | 5074036 B2 | 11/2012 |

(56) References Cited

FOREIGN PATENT DOCUMENTS

| | | | |
|---|---|---|---|
| JP | 2012531265 A | 12/2012 |
| JP | 2013503007 A | 1/2013 |
| JP | 5148284 B2 | 2/2013 |
| JP | 5198069 B2 | 5/2013 |
| JP | 2014000425 A | 1/2014 |
| KR | 20050072500 A | 7/2005 |
| KR | 20050084024 A | 8/2005 |
| KR | 20120090997 A | 8/2012 |
| KR | 20120102576 A | 9/2012 |
| MX | 2012007140 A | 1/2013 |
| NZ | 597261 A | 11/2013 |
| SG | 173840 A1 | 9/2011 |
| SG | 175229 A1 | 11/2011 |
| SG | 176833 A1 | 1/2012 |
| SG | 178836 A1 | 4/2012 |
| SG | 193484 A1 | 10/2013 |
| TW | 200509870 A | 3/2005 |
| TW | 1231755 B | 5/2005 |
| TW | 200800123 A | 1/2008 |
| TW | 1330075 B | 9/2010 |
| WO | 2004049981 A3 | 6/2004 |
| WO | 2004051301 A3 | 6/2004 |
| WO | 2005051239 A1 | 6/2005 |
| WO | 2005051240 A1 | 6/2005 |
| WO | 2006058057 A2 | 6/2006 |
| WO | 2006060795 A1 | 6/2006 |
| WO | 2006058057 A8 | 7/2006 |
| WO | 2007041375 A2 | 4/2007 |
| WO | 2007062103 A1 | 5/2007 |
| WO | 2007092841 A2 | 8/2007 |
| WO | 2007109641 A2 | 9/2007 |
| WO | 2007092841 A3 | 11/2007 |
| WO | 2007109641 A3 | 12/2007 |
| WO | 2008101090 A2 | 8/2008 |
| WO | 2008112996 A1 | 9/2008 |
| WO | 2008101090 A3 | 11/2008 |
| WO | 2008157412 A2 | 12/2008 |
| WO | 2007041375 A3 | 4/2009 |
| WO | 2008157412 A3 | 4/2009 |
| WO | 2009111626 A2 | 9/2009 |
| WO | 2009111639 A1 | 9/2009 |
| WO | 2009111656 A1 | 9/2009 |
| WO | 2009140294 A1 | 11/2009 |
| WO | 2009111626 A3 | 1/2010 |
| WO | 2010099231 A2 | 9/2010 |
| WO | 2010099353 A1 | 9/2010 |
| WO | 2010121147 A1 | 10/2010 |
| WO | 2010099231 A3 | 11/2010 |
| WO | 2011028624 A1 | 3/2011 |
| WO | 2011056995 A2 | 5/2011 |
| WO | 2011072235 A2 | 6/2011 |
| WO | 2011075697 A2 | 6/2011 |
| WO | 2011056995 A3 | 9/2011 |
| WO | 2011075697 A3 | 10/2011 |
| WO | 2011072235 A3 | 12/2011 |
| WO | 2012/027816 A1 | 3/2012 |
| WO | 2012112694 A1 | 8/2012 |
| WO | 2012112694 A2 | 8/2012 |
| WO | 2012112698 A2 | 8/2012 |
| WO | 2012112701 A2 | 8/2012 |
| WO | 2012112702 A2 | 8/2012 |
| WO | 2012112694 A3 | 1/2013 |
| WO | 2012112701 A3 | 1/2013 |
| WO | 2012112702 A3 | 1/2013 |
| WO | 2013020026 A1 | 2/2013 |
| WO | 2013025814 A1 | 2/2013 |
| WO | 2012112698 A3 | 3/2013 |
| WO | 2013056036 A1 | 4/2013 |
| WO | 2013119790 A1 | 8/2013 |
| WO | 2013119865 A1 | 8/2013 |
| WO | 2013131066 A1 | 9/2013 |
| WO | 2013152341 A1 | 10/2013 |
| WO | 2013155500 A1 | 10/2013 |
| WO | 2013155501 A1 | 10/2013 |
| WO | 2014008444 A1 | 1/2014 |
| WO | 2014035991 A1 | 3/2014 |
| WO | 2014047514 A1 | 3/2014 |

OTHER PUBLICATIONS

Hofmann et al, "Natural-Knee II System", Intermedics Orthopedics, Austin, TX, 1995.

* cited by examiner

PATIENT SPECIFIC INSTRUMENTATION WITH MEMS IN SURGERY

CROSS-REFERENCE TO RELATED APPLICATION

The present application claims priority on U.S. Provisional Application Ser. No. 61/675,242, filed on Jul. 24, 2012, and incorporated herewith by reference.

FIELD OF THE APPLICATION

The present application relates to the patient specific instrumentation and inertial sensors such as microelectromechanical sensors (MEMS) in orthopedic surgery.

BACKGROUND OF THE ART

One of the essential steps in navigating a bone and tools with MEMS sensors is to initially locate the bone relative to the sensors, i.e., creating a frame of reference or coordinate system. Some steps must be performed to create the frame of reference considering specifications of MEMS sensor systems. Specifications of MEMS sensor systems may include orientation tracking along two degrees of freedom only, or the absence of positional tracking. Known steps of calibration comprise various manipulations of a sensor and/or bone, for the orientational setting of the sensor (hereinafter, the reference tracker) with respect to the bone. Once the orientational setting is completed, navigation steps may be performed, with the bone being tracked via the frame of reference using the reference tracker.

In some instances, the sensor must be constrained with respect to a bone for subsequent tracking. For femur tracking for example, the orientation of the sensor relative to the lateral axis can be constrained mechanically (e.g., with claws inserted under the posterior condyles) so that the sensor lateral axis is aligned with the lateral axis of the bone.

In other instances, various tools used to perform alterations on a bone must be calibrated with respect to a MEMS reference tracker, to be tracked during navigation. One example is the cutting block (a.k.a., positioning block), which may be mechanically constrained to the MEMS reference tracker for the calibration to be made. In such known cases, specific manipulations must be executed by the operator to ensure that the positioning block is connected to the reference tracker for the calibration of the positioning block, for subsequent tracking and bone alterations.

Patient specific instrumentation (hereinafter "PSI") pertains to the creation of instruments that are made specifically for the patient, and that hence have a contact surface(s) that is a negative of the bone surface to which it will be anchored. Hence, when the contact surface of the PSI is positioned against the bone, there is complementary contact (the contact surface negatively matching the anchor surface). PSI are typically manufactured from data using imagery to model bone geometry and thus be a true negative. The complementary engagement is predictable as such contact surfaces are specifically manufactured to match the surface of a bone. It would therefore be desirable to use PSI technology with MEMS.

SUMMARY OF THE APPLICATION

It is therefore an aim of the present disclosure to provide a novel method and patient specific instrumentation for tracking bones and tools using MEMS in surgery.

Therefore, in accordance with a first embodiment of the present disclosure, there is provided a method for creating a patient specific instrument model with an inertial sensor unit, comprising: obtaining a patient specific bone model of at least part of a bone; identifying at least one contact surface of the bone; identifying orientation data related to the bone, a geometrical relation between the at least one contact surface and the orientation data being known; generating a patient specific instrument model having at least one surface negatively corresponding to the at least one contact surface of the bone; defining a connection configuration for an inertial sensor unit in the patient specific instrument model using said geometrical relation, the connection configuration relating a preset orientation of the inertial sensor unit to the orientation data of the bone; and outputting the patient specific instrument model with the connection configuration for receiving the inertial sensor unit.

Further in accordance with the first embodiment, identifying orientation data related to the bone comprises identifying at least one axis of the bone.

Still further in accordance with the first embodiment, identifying orientation data related to the bone comprises scanning the bone while in a known orientation relating the ground, identifying at least one axis of the bone, generating the patient specific bone model from the scanning, and relating the known orientation to the patient specific bone model.

Still further in accordance with the first embodiment, defining a connection configuration comprises aligning an axis from the preset orientation of the inertial sensor unit with an axis of said orientation data.

Still further in accordance with the first embodiment, wherein outputting the patient specific instrument model comprises outputting a receptacle in the patient specific instrument model for receiving the inertial sensor unit in the connection configuration.

In accordance with a second embodiment of the present disclosure, there is provided a method for tracking a bone with a patient specific instrument with an inertial sensor unit, comprising: obtaining a patient specific instrument with an inertial sensor unit, the inertial sensor unit being preset with orientation data related to the bone; placing the patient specific instrument on the bone by complementary contact between a surface of the bone and a negative patient specific surface of the patient specific instrument; initializing the inertial sensor unit in the complementary contact to relate the orientation data to the bone; and tracking the bone using data provided by the inertial sensor unit.

Still further in accordance with the second embodiment, initializing the inertial sensor unit comprises aligning an axis of the orientation data of the inertial sensor unit with an axis of the bone obtained with the patient specific instrument.

Still further in accordance with the second embodiment, obtaining a patient specific instrument with an inertial sensor unit comprises obtaining the patient specific instrument with the inertial sensor unit separately, and further comprising connecting the inertial sensor unit to the patient specific instrument in a known connector configuration.

In accordance with a third embodiment of the present disclosure, there is provided an assembly of a patient specific instrument and tracking system comprising: a patient specific instrument having a body with a patient specific contact surface negatively shaped relative to a corresponding surface of a bone for complementary contact therewith, and an inertial sensor unit with a preset orientation, the inertial sensor unit being connected to the body in a planned connection configuration, such that a geometrical relation between the contact surface and the inertial sensor unit is known; and a tracking system having a tracking processor connected to the inertial sensor unit, a user interface, and bone orientation data related to the patient specific contact surface, the tracking processor producing orientation tracking data for the bone using the geometrical relation and the bone orientation data when the preset orientation of the inertial sensor unit is initialized, to output the orientation tracking data on the user interface.

Further in accordance with the third embodiment, the patient specific instrument comprises a tool interface in the body, with a geometrical relation between the tool interface and the inertial sensor unit being known.

Still further in accordance with the third embodiment, the tool interface is one of a cut guide and a drill guide.

Still further in accordance with the third embodiment, the bone orientation data is a file comprising at least one axis of the bone.

Still further in accordance with the third embodiment, the body comprises a receptacle for releasably receiving the inertial sensor in the connection configuration.

DESCRIPTION OF THE EXEMPLARY
EMBODIMENTS

Figure 1:
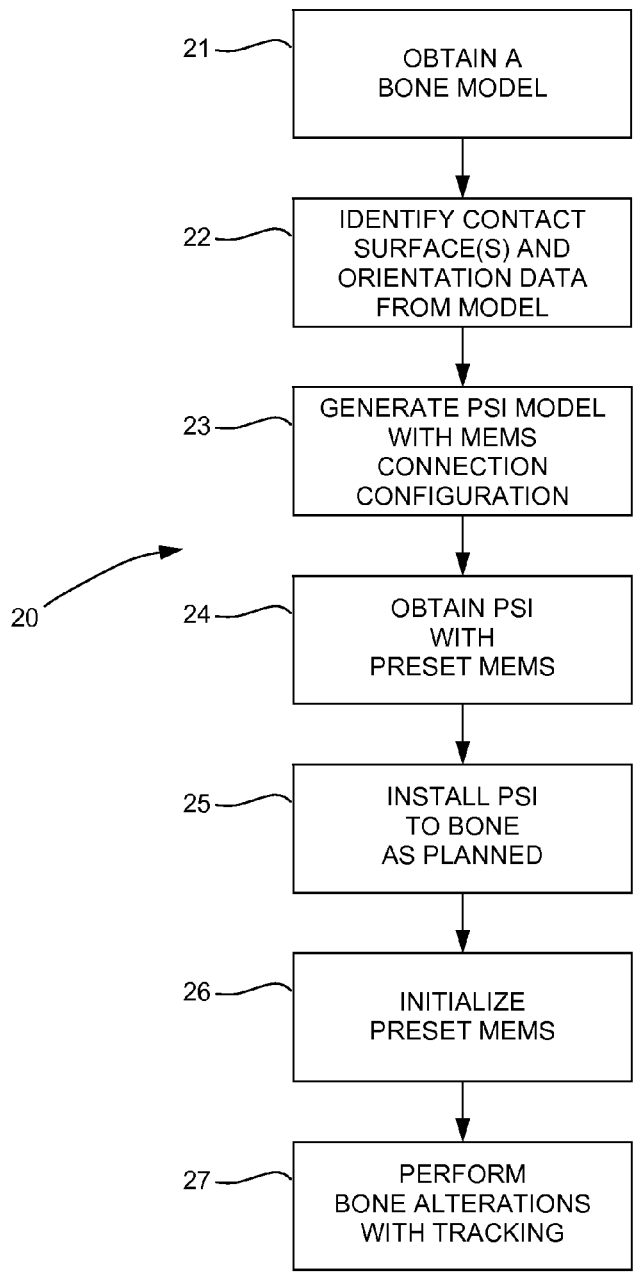
FIG. 1 is a flowchart of a method for creating a patient specific instrument model with a preset MEMS unit, and for tracking bones using same, in accordance with the present disclosure.

Referring to the drawings and more particularly to FIG. 1, there is provided a method for creating a patient specific instrument model with a preset microelectromechanical sensors unit, and for tracking a bone using same. The microelectromechanical sensors unit (hereinafter MEMS unit, a.k.a., inertial sensor unit) produces readings pertaining to at least two degrees of freedom (DOFs) in orientation (rotation about axes), although the MEMS could provide readings for more degrees of freedom, in orientation and/or translation, if appropriately equipped. The MEMS unit may comprise a gyroscope and/or accelerometer, or sets thereof, among other possibilities. The MEMS unit may be of the preset type, in that it is preset with axes whose orientation are known relative to landmarks when the MEMS unit is initialized (i.e., initially turned on).

Referring to FIG. 1, a method 20 is illustrated for the creation of the PSI and initialization thereof for subsequent surgical steps to be performed on the bone.

According to a first sequence of steps, PSI model generation planning is performed. The first sequence of steps results in the creation of a PSI model for subsequent manufacturing of the PSI according to the present disclosure.

According to step 21, a bone model is obtained. The bone model is typically a 3-D model that is created from pre-operative imagery (e.g., CT scans, etc) and model generation, and is hence patient specific as it is a physiological model of the specific patient's bone/cartilage. Depending on the number of bones involved in the surgery, step 21 may involve the creation of more than one patient specific bone model. Moreover, although reference is made to a bone model, it should be understood that the models may be for parts of a bone, as opposed to the complete bone. The generation of the model may include cartilage and/or other anatomical material. The imaging may be done by any appropriate technology such as CT scanning (computerized tomography), fluoroscopy, or like radiography methods, providing suitable resolution of images. It is also considered to use other methods to generate the bone model, such as digitizing points on the bone, etc.

According to step 22, contact surfaces are identified on the bone from the model(s) of 21. The anchor surfaces are selected as being sufficiently large to support a PSI. Moreover, the PSI may be anchored (e.g., screwed, fastened) to the bone whereby the contact surface or adjacent surfaces should be capable of being altered (e.g., pierced, drilled).

Still in step 22, orientation data is obtained from the model(s) of step 21. More specifically, the orientation data may be axes of the modeled bone, rotational axes of a joint, etc. As the orientation data is obtained from the patient specific bone model, the orientation data is also specific to the patient. The 3-D models of step 21 or like images (e.g., 2-D images) may provide sufficient resolution or data to identify this orientation data. For instance, bone landmarks may be visible from the images of step 21 to obtain this orientation data. Alternatively, landmarks may be taken manually directly on the bone (e.g., using tracking devices, etc), and the orientation data may be obtained with these landmarks. It is pointed out that the geometrical relation between the orientation data and the contact surfaces is known, as this geometrical relation is obtained from images of step 21, or from any manual operation performed for this purpose.

According to an embodiment, the bone model of step is obtained from a pre-operative scan (e.g., in a MRI, calibrated X-ray or CT-Scan) in which the bone is in a known relationship with respect to the ground. A 3D model of the bone is obtained from the images, but the relationship to ground is maintained, and is used in step 22 as orientation data. This may be performed for one or more bones. With multiple bones, the orientation data may comprise geometrical data relating bones to one another.

According to step 23, using the contact surfaces and orientation data as obtained from the bone model(s) and/or manipulations, and the geometrical relation between the contact surfaces and the orientation of the bone, a PSI model is generated. The PSI model will have a negative contact surface(s) defined to complementarily abut against the contact surface(s) obtained in step 22, in a predictable and precise manner.

Moreover, the PSI model may have a connection configuration for receiving any appropriate MEMS unit, if the MEMS unit is to be provided as a separate component attachable to the PSI resulting from the PSI model. The connector configuration of the PSI model is defined using the orientation data of step 22 and the geometrical relation between the orientation data and the contact surface(s). For instance, the connection configuration may be a receptacle defined in the PSI for receiving a preset MEMS unit. The connection configuration is defined such that the orientation of the MEMS unit is known relative to the PSI when the MEMS unit is installed in the PSI, and therefore known relative to the contact surface(s) and to the orientation data. In other words, when the MEMS unit is initialized, its orientation along at least one axis will be known relative to the PSI. If the PSI is secured to the bone in the planned manner (step 22), the initialization of the MEMS unit will result in the automatic calibration of the MEMS unit relative to the orientation of the bone to which the PSI connected.

According to an embodiment, the PSI may be used with other components and/or tools. For instance, the PSI may incorporate or support a cutting block or cutting guide that will allow to cut planes upon which will be anchored the implant. The PSI model of step 23 may therefore comprise cutting planes, guides, slots, or any other tooling interface or tool, oriented and/or positioned to allow bone alterations to be formed in a desired location of the bone, relative to the contact surface(s). Thus, PSI model may also take into consideration any planning done by the operator (e.g., surgeon), to therefore allow the removal of sufficient bone material to reproduce desired gaps between cut planes on adjacent bones, etc.

Once the PSI model has been generated, the PSI may be created. The PSI incorporates a preset MEMS unit or the preset MEMS unit may be separate, but in both cases the connection configuration between the PSI and MEMS unit is known.

According to a second sequence of steps, the surgery may be performed. According to step 24, the PSI with the preset MEMS unit may be obtained by the surgeon or operator.

According to step 25, the PSI with preset MEMS unit may be installed on the bone as planned. Therefore, when installing the PSI on the bone, the negative contact surface(s) on the PSI (as discussed in step 22) is(are) applied against the corresponding surface(s) of the bone. The complementary engagement of the negative contact surface and the bone will self-align the placement of the PSI. Accordingly, by installing the PSI as planned, the orientation data preset into the MEMS unit of the PSI (step 22) may be transposed to the bone.

Therefore, according to step 26, the preset MEMS unit may be initialized. When the MEMS unit of the PSI is ready to be initialized, the PSI has been secured to the bone. At the moment at which the MEMS unit on the PSI is initialized, the relation is established between the bone and the orientation data preset into the MEMS unit. From this point on, the orientation may be tracked for the bone from the readings of the initialized MEMS unit.

In the embodiment at which the orientation data comprises an orientation relative to the ground, it is possible to track the position and/or orientation of the bone in space relative to the ground plane provided by the pre-operative imaging. It is also possible to know the relative position and/or orientation of one bone with respect to the other. In this configuration, the movement of one bone may be navigated with respect to the other, giving range-of-motion data.

According to step 27, bone alterations may be performed using the tracking provided by the initialized MEMS unit. Step 27 may comprise the connection of additional components on the PSI, the use of the PSI as a guide, etc. As an alternative, step 27 may comprise additional calibration steps to confirm that the orientation data produced by the MEMS unit accurately represents the actual orientation of the bone. For instance, various methods have been developed and described to create frames of reference using MEMS reference trackers for tracking of bones, for the subsequent tracking of the bones. A method is described in United States Patent Application Publication No. 2009/0247863, published on Oct. 1, 2009, incorporated herein by reference. Another method is described in United States Patent Application Publication No. 2009/0248044, published on Oct. 1, 2009, incorporated herein by reference. Yet another method is described, for a femoral application, in U.S. patent application Ser. No. 12/846,934, filed on Jul. 30, 2010, also incorporated herein by reference. Of interest in these references are the methods and systems to create a frame of reference (e.g., a coordinate system) with a MEMS sensor unit (i.e., reference tracker) with respect to a bone for the subsequent tracking of the bone in orientation Any of the methods described in these patent applications and, more importantly, simplifications thereof, may be performed to confirm that the orientation data provided by the MEMS unit accurately represents the actual orientation of the bone. For instance, if a prior art method requires multiple points to be obtained, it may be possible to obtain fewer points in such methods as these methods would be use as a validation.

In other words, tools or references with MEMS unit may be fixed to the bone, and then the relationship to the contact surface of the PSI may be used to shorten the usual MEMS registration process (for instance less points to digitize on the femur). This can be done if PSI cannot provide enough accuracy, but could be used to substantially simplify the registration of bones.

It is pointed out that the aforedescribed method may be performed on bone models or cadavers. The sequence of steps of the method may also be in any other suitable order.

In one embodiment, the MEMS unit of the cutting block is a "zero" initial orientation for each rotational axis it tracks. In the "zero" initial orientation, the rotational axes are orthogonal to the MEMS unit of the PSI. Other initial configurations are possible as well.

Figure 2:
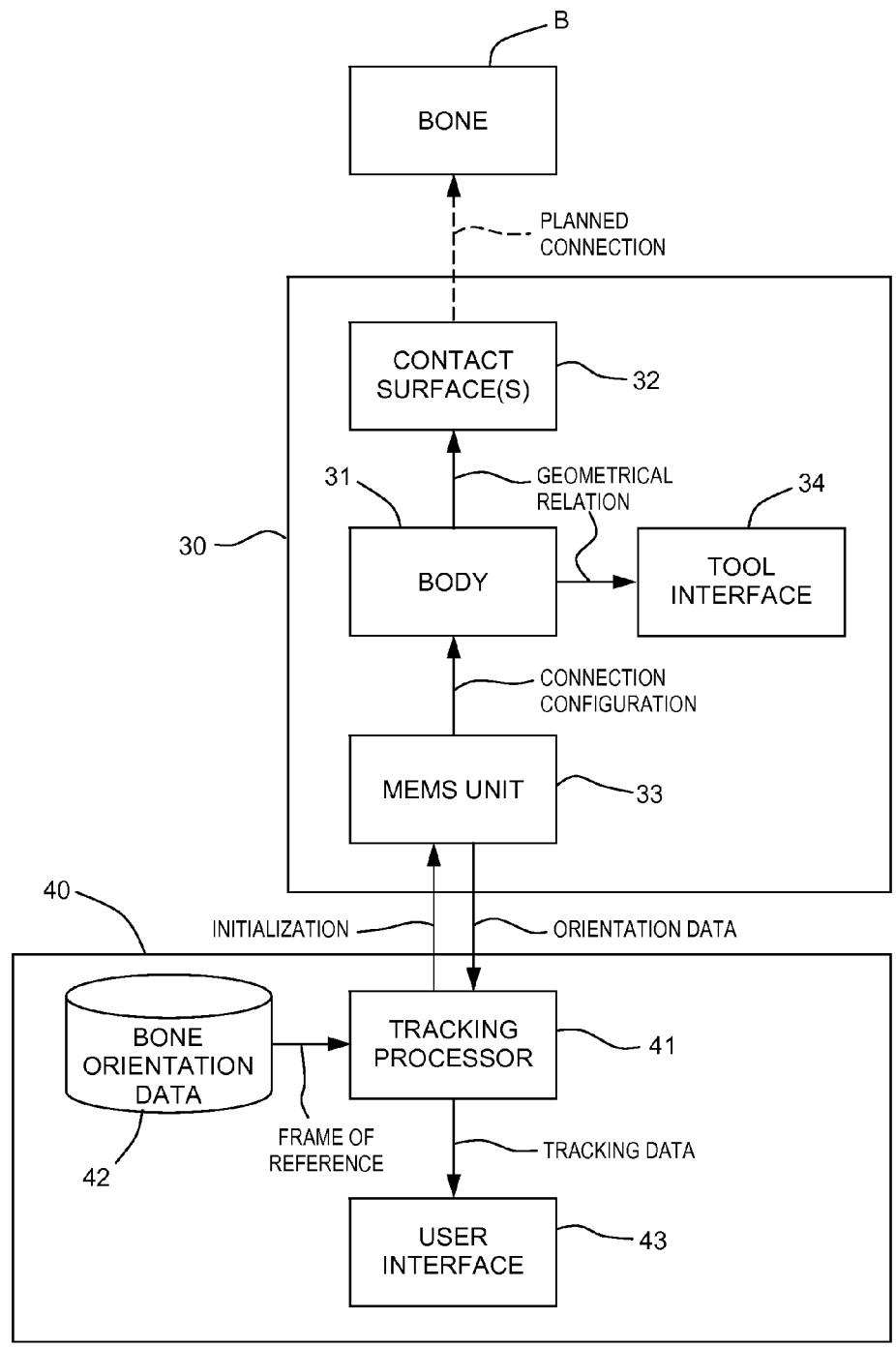
FIG. 2 is a block diagram of a patient specific instrument with MEMS unit and tracking processor, in accordance with the present disclosure.

Referring now to FIG. 2, there is illustrated at 30 a PSI of the type created and used in the method 20 of FIG. 1. The PSI 30 comprises a body 31. The body 31 has a negative contact surface 32 (or contact surfaces 32) specifically manufactured for the patient (i.e., it is patient specific), so as to marry the shape (i.e., complementarily contact) of a bone contact surface of bone B, as planned. A MEMS unit 33, of the type being preset in orientation, is also within the body 31, or may be connectable in a predetermined manner to the body 31 in a receptacle defined in the body and adapted to receive the MEMS unit 33 is a precise and predictable manner. When the body 31 is manufactured, the connection configuration of the MEMS unit 33 therein is also planned such that in orientation of the MEMS unit 33 is known relative to a geometry of the body 31. The body 31 may comprise a tool interface 34, which may also be planned, the tool interface 34 used with tools to perform alterations on the bone. The tools may be any appropriate tool conventionally used for orthopedic surgery.

The PSI 30 is used with a tracking system 40. The tracking system 40 may be integrated in the body 31 or separate therefrom. The tracking system 40 comprises a tracking processor 41 that receives orientation data from the MEMS unit 33. Bone orientation data 42 is provided in the tracking system 40, and results from planning, for instance as set forth in steps 21 to 23 of the method 20 of FIG. 1. Bone orientation data 42 comprises a frame of reference for the bone (e.g., axes) in relation to the contact surface 32, and in relation to the connection configuration between the body 31 and the MEMS unit 33 in the PSI 30. Hence, when the MEMS unit 33 is initialized (i.e. initially turned on), the tracking processor 41 uses the bone orientation data 42 to set the orientation data of the bone with respect to the readings provided by the MEMS unit 33. The tracking system 40 comprises a user interface 43 of any suitable type to provide data to the user relative to the orientation of the bone as tracked.

While the methods and systems described above have been described and shown with reference to particular steps performed in a particular order, these steps may be combined, subdivided or reordered to form an equivalent method without departing from the teachings of the present disclosure. Accordingly, the order and grouping of the steps is not a limitation of the present disclosure. The methods and systems described above may be used for any appropriate type of orthopaedic surgery (knee, shoulder, hip, resurfacing, replacement, revision), with any suitable type of bone, such as the tibia, femur, humerus, pelvis, etc.

The invention claimed is:

1. An assembly of a patient specific instrument and tracking system comprising:
   a patient specific instrument having a body with a patient specific contact surface negatively shaped relative to a corresponding surface of a bone for complementary contact therewith, and an inertial sensor unit programmed with a preset virtual orientation, the inertial sensor unit being received in a receptacle on the body to be fixedly connected to the body in a planned connection configuration, such that a geometrical relation between the contact surface and the inertial sensor unit is known when the body and the inertial sensor unit are fixed to the bone; and
   a tracking system having a tracking processor connected to the inertial sensor unit, a user interface, and bone orientation data related to the patient specific contact surface, the tracking processor producing orientation tracking data for the bone using the geometrical relation and the bone orientation data when the preset virtual orientation of the inertial sensor unit is initialized, to output the orientation tracking data on the user interface.

2. The assembly according to claim 1, wherein the patient specific instrument comprises a tool interface in the body, with a geometrical relation between the tool interface and the inertial sensor unit being known.

3. The assembly according to claim 2, wherein the tool interface is one of a cut guide and a drill guide.

4. The assembly according to claim 1, wherein the bone orientation data is a file comprising at least one axis of the bone.

5. The assembly according to claim 1, wherein the body comprises a receptacle for releasably receiving the inertial sensor in the connection configuration.

* * * * *